United States Patent [19]
Chartrain et al.

[11] Patent Number: 6,121,026
[45] Date of Patent: Sep. 19, 2000

[54] ENANTIOSELECTIVE BIOREDUCTION USING YEAST

[75] Inventors: Michel M. Chartrain, Westfield; Barbara A. Krulewicz, Bloomfield; Paul N. Devine, Lincroft; David M. Tschaen, Holmdel, all of N.J.

[73] Assignee: Merck & Co., Inc., Rahway, N.J.

[21] Appl. No.: 09/360,202

[22] Filed: Jul. 23, 1999

Related U.S. Application Data

[60] Provisional application No. 60/095,679, Aug. 7, 1998.

[51] Int. Cl.⁷ .............................. C12P 7/00; C07D 317/44
[52] U.S. Cl. ............................................. 435/132; 549/445
[58] Field of Search ............................... 435/132; 549/445

[56] References Cited

U.S. PATENT DOCUMENTS

| | | | |
|---|---|---|---|
| 4,147,799 | 4/1979 | Obase et al. ............................ | 424/282 |
| 5,717,116 | 2/1998 | Saito et al. ............................. | 549/522 |

OTHER PUBLICATIONS

Obase, H. et al "1–(3,4–methylenedioxyphenyl)–2–alkylaminoethanol Derivatives" CA 78:136260 (1973).

Saito, K. et al "Process for Producing (R)–Styrene Oxides" CA 125:273737 (1991).

*Primary Examiner*—Amelia Owens
*Attorney, Agent, or Firm*—Valerie J. Camara; Mark R. Daniel

[57] ABSTRACT

The invention relates to a class of enantiomerically pure intermediates represented by Formula I, where X is F, Cl, Br, or I, and a novel enantioselective bioreductive process using yeast to form these intermediates, which are useful in the synthesis of endothelin antagonists, and the like.

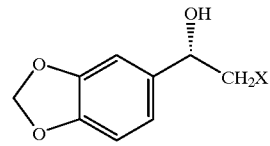

I

2 Claims, No Drawings

ENANTIOSELECTIVE BIOREDUCTION USING YEAST

This non-provisional application claims priority from provisional application U.S. Ser. No. 60/095,679, filed Aug. 7, 1998 (now abandoned).

BACKGROUND OF THE INVENTION

The present invention relates to a novel enantioselective bioreductive process using yeast to form intermediates in the synthesis of an endothelin antagonist, and the like.

Two endothelin receptor subtypes $ET_A$ and $ET_B$ are known. These receptors are responsible for the dilation of smooth muscle, such as blood vessels or in the trachea. Endothelin antagonist compounds provide a new therapeutic potential, particularly for the treatment of hypertension, pulmonary hypertension, Raynaud's disease, acute renal failure, myocardial infarction, angina pectoris, cerebral infarction, cerebral vasospasm, arteriosclerosis, asthma, gastric ulcer, diabetes, restenosis, prostatauxe endotoxin shock, endotoxin-induced multiple organ failure or disseminated intravascular coagulation, and/or cyclosporin-induced renal failure or hypertension.

Endothelin is a polypeptide composed of amino acids, and it is produced by vascular endothelial cells of human or pig. Endothelin has a potent vasoconstrictor effect and a sustained and potent pressor action (*Nature*, 332, 411–415 (1988)).

Three endothelin isopeptides (endothelin-1, endothelin-2 and endothelin-3), which resemble one another in structure, exist in the bodies of animals including human, and these peptides have vasoconstriction and pressor effects (Proc. Natl. Acad, Sci, USA, 86, 2863–2867 (1989)).

As reported, the endothelin levels are clearly elevated in the blood of patients with essential hypertension, acute myocardial infarction, pulmonary hypertension, Raynaud's disease, diabetes or atherosclerosis, or in the washing fluids of the respiratory tract or the blood of patients with asthmaticus as compared with normal levels (Japan, J. Hypertension, 12, 79, (1989), J. Vascular medicine Biology, 2, 207 (1990), Diabetologia, 33, 306–310 (1990), J. Am. Med. Association, 264, 2868 (1990), and The Lancet, ii, 747–748 (1989) and ii, 1144–1147 (1990)).

An increased sensitivity of the cerebral blood vessel to endothelin in an experimental model of cerebral vasospasm (Japan. Soc. Cereb. Blood Flow & Metabol., 1 73 (1989)), an improved renal function by the endothelin antibody in an acute renal failure model (J. Clin, invest., 83, 1762–1767 (1989), and inhibition of gastric ulcer development with an endothelin antibody in a gastric ulcer model (Extract of Japanese Society of Experimental Gastric Ulcer, 50 (1991)) have been reported. Therefore, endothelin is assumed to be one of the mediators causing acute renal failure or cerebral vasospasm following subarachnoid hemorrhage.

Endothelin is secreted not only by endothelial cells but also by tracheal epithelial cells or by kidney cells (FEBS Letters, 255, 129–132 (1989), and FEBS Letters, 249, 42–46 (1989)). Endothelin was also found to control the release of physiologically active endogenous substances such as renin, atrial natriuretic peptide, endothelium-derived relaxing factor (EDRF), thromboxane $A_2$, prostacyclin, noradrenaline, angiotensin II and substance P (Biochem. Biophys, Res. Commun., 157, 1164–1168 (1988); Biochem. Biophys, Res. Commun., 155, 20 167–172 (1989); Proc. Natl. Acad. Sci. USA, 85 1 9797–9800 (1989); J. Cardiovasc. Pharmacol., 13, S89–S92 (1989); Japan. J. Hypertension, 12, 76 (1989) and Neuroscience Letters, 102, 179–184 (1989)). Further, endothelin causes contraction of the smooth muscle of gastrointestinal tract and the uterine smooth muscle (FEBS Letters, 247, 337–340 (1989); Eur. J. Pharmacol., 154, 227–228 (1988); and Biochem. Biophys Res. Commun., 159, 317–323 (1989)). Endothelin was also found to promote proliferation of rat vascular smooth muscle cells, suggesting a possible relevance to the arterial hypertrophy (Atherosclerosis, 78, 225–228 (1989)). Since the endothelin receptors are present in a high density not only in the peripheral tissues but also in the central nervous system, and the cerebral administration of endothelin induces a behavioral change in animals, endothelin is likely to play an important role for controlling nervous functions (Neuroscience Letters, 97, 276–279 (1989)). Particularly, endothelin is suggested to be one of mediators for pain (Life Sciences, 49, PL61–PL65 (1991)).

Internal hyperplastic response was induced by rat carotid artery balloon endothelial denudation. Endothelin causes a significant worsening of the internal hyperplasia (J. Cardiovasc. Pharmacol., 22, 355–359 & 371–373(1993)). These data support a role of endothelin in the phathogenesis of vascular restenosis. Recently, it has been reported that both $ET_A$ and $ET_B$ receptors exist in the human prostate and endothelin produces a potent contraction of it. These results suggest the possibility that endothelin is involved in the pathophysiology of benign prostatic hyperplasia (J. Urology, 151, 763–766(1994), Molecular Pharmocol., 45, 306–311 (1994)).

On the other hand, endotoxin is one of potential candidates to promote the release of endothelin. Remarkable elevation of the endothelin levels in the blood or in the culture supernatant of endothelial cells was observed when endotoxin was exogenously administered to animals or added to the culture endothelial cells, respectively. These findings suggest that endothelin is an important mediator for endotoxin-induced diseases (Biochem. Biophys. Commun., 161, 1220–1227 (1989); and Acta Physiol. Scand., 137, 317–318 (1989)).

It has been reported that cyclosporin remarkably increased endothelin secretion in the renal cell culture (LLC-PKL cells) (Eur. J. Pharmacol., 180, 191–192 (1990)). Dosing of cyclosporin to rats reduced the glomerular filtration rate and increased the blood pressure in association with a remarkable increase in the circulating endothelin level. This cyclosporin-induced renal failure can be suppressed by the administration of endothelin antibody (Kidney Int., 37, 1487–1491 (1990)). Thus, it is assumed that endothelin is significantly involved in the pathogenesis of the cyclosporin-induced diseases.

Such various effects of endothelin are caused by the binding of endothelin to endothelin receptors widely distributed in many tissues (Am. J. Physiol., 256, R856–R866 (1989)). It is known that vasoconstriction by the endothelins is caused via at least two subtypes of endothelin receptors (J.

Cardiovasc. Pharmacol., 17(Suppl.7), S119–SI21 (1991)). One of the endothelin receptors is $ET_A$ receptor Selective to ET-1 rather than ET-3, and the other is $ET_B$ receptor equally active to ET-1 and ET-3. These receptor proteins are reported to be different from each other (Nature, 348, 730–735 (1990)).

These two subtypes of endothelin receptors are differently distributed in tissues. It is known that the $ET_A$ receptor is present mainly in cardiovascular tissues, whereas the $ET_B$ receptor is widely distributed in various tissues such as brain, kidney, lung, heart and vascular tissues.

Substances which specifically inhibit the binding of endothelin to the endothelin receptors are believed to antagonize various pharmacological activities of endothelin and to be useful as a drug in a wide field. Since the action of the endothelins is caused via not only the $ET_A$ receptor but also the $ET_B$ receptor, novel non-peptidic substances with ET receptor antagonistic activity to either receptor subtype are desired to block activities of the endothelins effectively in various diseases. Several such compounds are known. For example, U.S. Pat. No. 5,565,485, issued Oct. 15, 1996, teaches a compound of Formula 9 which is useful as an endothelin anatagonist.

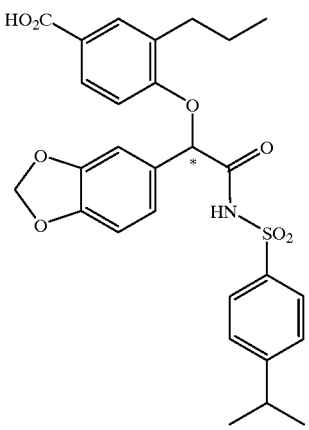

9

Compound 9, however, contains an asymmetric center represented with "*" above and stereoselective synthetic routes remain desireable.

SUMMARY OF THE INVENTION

The present invention relates to a class of enantiomerically pure intermediates represented by Formula I, where X is F, Cl, Br, or I, and a novel enantioselective bioreductive process using yeast to form these intermediates, which are useful in the synthesis of endothelin antagonists, and the like.

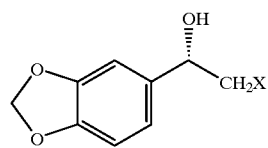

I

DETAILED DESCRIPTION OF THE INVENTION

An embodiment of the invention is a process for the preparation of a compound of Formula I

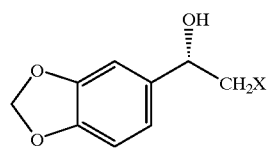

I comprising the step of culturing a microorganism, *Rhodotorula piliminae*, (ATCC 32762), in a nutrient medium containing assimilable sources of nitrogen and carbon and a substrate compound of Formula II,

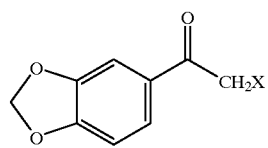

II wherein X is F, Cl, Br, or I.

A preferred embodiment of the invention is the process described above wherein X is Cl.

Yet another embodiment of the invention is a compound of Formula I,

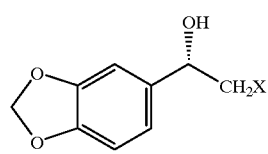

I wherein X is F, Cl, Br, or I.

A preferred embodiment of the invention is the compound of Formula I wherein X is Cl.

The racemic synthesis and utility of endothelin antagonist 9 below has been previously published in U.S. Pat. No. 5,565,485, issued Oct. 15, 1996, which is hereby incorporated by reference.

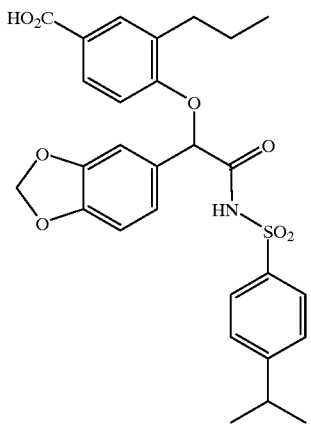

Modification of the racemic synthesis taught in U.S. Pat. No. 5,565,485, according to the following schemes produces the desired endothelin antagonist stereoselectively.

The substrates necessary for the claimed bioreductive process, such as chloroketone 12, can be obtained by the procedure outlined in Scheme 1 below using chemical procedures that are well known in the art. The starting bromide, 4-bromo-1,2-(methylenedioxy)benzene is commercially available from Aldrich Chemical Co. in Milwaukee, Wis., for example.

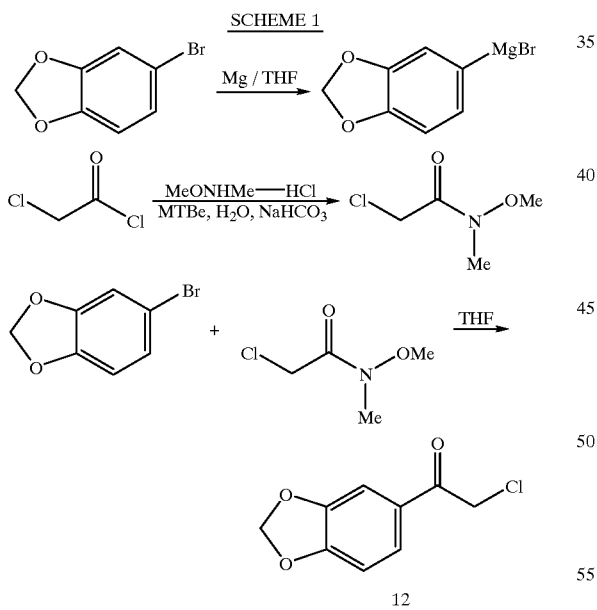

As shown in Scheme 2 below, chlorohydrin 1, obtained from the claimed bioreductive process using compound 12 as the substrate, is treated with potassium carbonate in THF at ambient temperature to give epoxide 2 in near quantitative yield. The epoxide is reacted with phenol 3 in the presence of a catalytic amount of titanium isopropoxide to give alcohol 4 with approximately 10–20% loss in enantioselectivity.

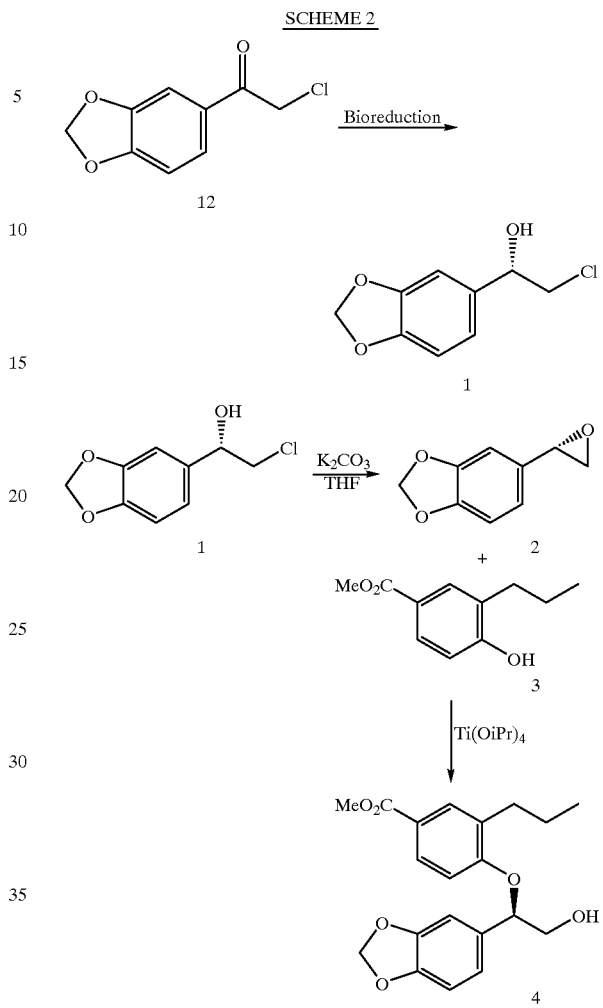

Alcohol 4 is then readily oxidized to the corresponding carboxylic acid 5 utilizing either TPAP or NaIO$_4$ with a catalytic amount of RuCl$_2$ as exemplified in Scheme 3 below. The next stage of the synthesis involves activation of the carboxylic acid 5 with a carboxyl-activating agent such as N,N-carbonyldiimidazole (CDI). This reaction is conducted in an aprotic solvent at elevated temperature such as refluxing THF, and an intermediate acyl-imidazole is formed, however this reactive intermediate is not isolated. The reaction mixture is cooled to room temperature briefly and the sulfonamide 6 and a base such as 1,8-diazabicyclo[5.4.0]undec-7-ene (DBU) is added. After reaction at elevated temperature for an additional period (1–6 hours) the coupling of the carboxylic acid 5 and the sulfonamide 6 is generally complete and the reaction mixture is cooled to room temperature. Partitioning the reaction mixture between an organic solvent like ethyl acetate or diethylether followed by extraction of the residual organic bases into dilute aqueous acid affords the semi-purified coupled product in the organic layer. This product can be isolated conveniently as an alkali metal salt (7) by evaporation of the organic layer from the previous step followed by treatment of the residue with one equivalent of sodium or potassium hydroxide in methanol. The synthesis of 8 is then completed by reaction of 7 with excess sodium or potassium hydroxide in a solvent such as methanol at room temperature or at moderately elevated temperatures such as 60° C. Hydrolysis of the remaining ester group in 7 affords the product 8. This organic diacidic compound (8) may also be isolated in pure form by crystallization of the semi-purified product with two equivalents of sodium or potassium hydroxide in a solvent such as methanol or ethanol.

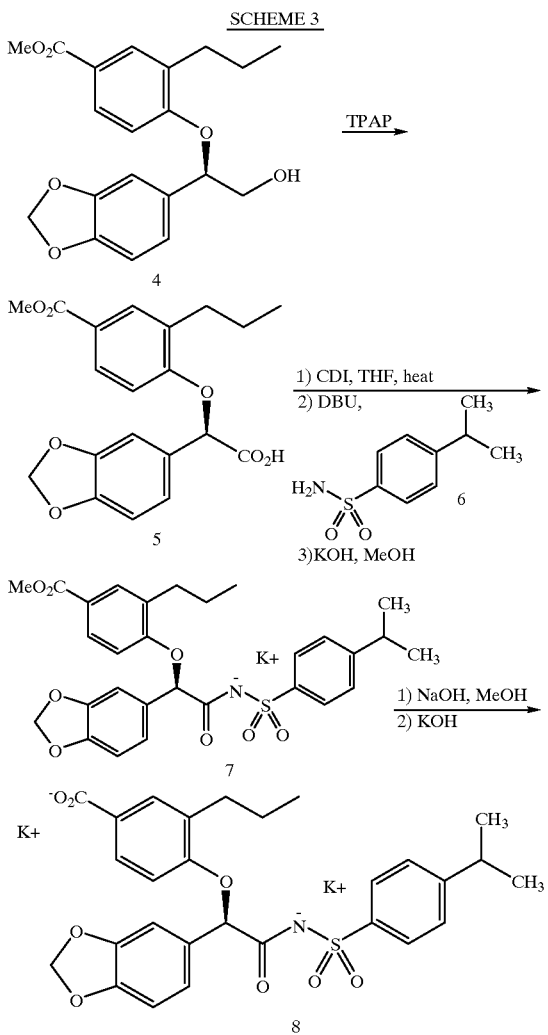

Microorganism *Rhodotorula piliminae*(ATCC 32762)

A biologically pure sample of *Rhodotorula piliminae* is isolated from the larva of *Drosophila pilimanae*, Hawaii and is currently available under the Budapest Treaty in the permanent culture collection of the American Type Culture Collection, 12301 Parklawn Drive in Rockville, Md., from which it is available under the Accession Number ATCC 32762.

The following examples illustrate the preparation of the compounds of Formula I and as such are not to be considered as limiting the invention set forth in the claims appended hereto.

EXAMPLE 1

Preparation of Stock Culture

Microbial strains were preserved as frozen suspensions in 20% glycerol at −70 C. A 1 mL volume of the frozen suspensions was used to inoculate 250-mL Erlenmeyer flasks containing 25 mL of Sabouraud Dextrose broth. After 48 h of incubation at 28° C. on a shaker operated at 220 rpm, a 1 mL or a 10 mL aliquot of each culture was used to inoculate a 250-mL Erlenmeyer flask containing 50 mL of Sabouraud Dextrose broth or a 2 L flask containing 500 mL of SDB. SDB contained (per L of water): Bacto Neopeptone, 10 g, and Bacto Dextrose, 20 g. The final pH of this medium was 5.6 and it was autoclaved for 20 min at 121 C. The medium was then incubated under the above described conditions for the specified time.

EXAMPLE 2

Fermentation Conditions

A 23-liter bioreactor (Chemap, South Plainfield, N.J.) was batched with 15 L of Sabouraud dextrose medium containing 2 mL/L of P 2000. The medium was sterilized in situ at 123° C. for 35 min. The fermentor was then inoculated with 500 mL of a 48 hr shake flask culture from Example 1 above. The bioreactor was operated with a 400 rpm agitation, a 0.5 bar back pressure and sparged air at a rate of 6–8 l/min. The temperature was maintained at 28° C. and dissolved oxygen concentration was maintained above 50% by cascade control of the agitator. pH was not controlled. Between 22–24 hours after inoculation, the substrate solution (16 gms of substrate dissolved in 144 mL DMSO) was added to give a final concentration of 1 g/L.

EXAMPLE 3

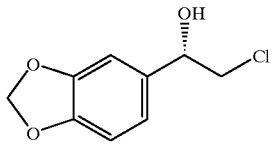

A 15-L fermentation was run with ATCC 32762 in Sabouraud Dextrose broth. 500 mL of a 24 hour culture was used to inoculate the tank. At 24 hours after inoculation, substrate ketone 12 was added to a final concentration of 1000 mg/L. The fermentation was stopped 22 hours after substrate addition, obtaining approximately 98% bioconversion and a final ee of 99%. The final product concentration obtained was 0.98 g/L. $^1$H NMR: d 3.5 (m, 2H), 4.8 (dd, 1H), 5.93 (s, 2H), 6.8 (m, 3H). Spectra was recorded at 400 MHz in $CD_2Cl_2$ on a Varian Unity 400 NMR spectrometer at 25° C. Chemical shifts are in ppm relative to TMS at zero ppm using the solvent peak at d5.32 as the internal standard.

Assay to Determine Bioconversion

The broth sample was extracted 1:5 in acetonitrile and the supernatant was analyzed directly by reverse plase HPLC analyses using a Zorbax RX C8 column (available from Fisher Scientific in Springfiled, N.J.). Separation was achieved by using a gradient of acetonitrile:water, 40/60 (v/v) to 90/10 (v/v) over 15 minutes, and held for 10 minutes. The system was re-equilibrated back to 40/60 (v/v)

for 5 minutes before the next injection. The flow rate was 1.0 mL/min and detection was performed at 220 nm at ambient temperature. The alcohol and ketone eluted after 10.8 and 12.6 min, respectively.

Assay to Determine Enantiomeric Excess

The broth sample was extracted 1:1 in ethyl acetate, centrifuged and dried. Acetonitrile was then added to resuspend the product. This sample was then filtered into HPLC vials and dried with nitrogen. 0.1 mL of methylene chloride was then added to each vial and spotted onto thin layer chromatography plates. The sample was eluted from the TLC plates using a mobile phase consisting of 100 mL ethyl acetate: 200 mL hexane. The product was scraped off the plates, extracted in 15 mL ethyl acetate, centrifuged 10 minutes, and the supernatant was collected and dried overnight. 2 mL of IPA were added to each beaker and the sample was then filtered into LC vials. 1:10 dilutions of these samples were run on a ChiralCell OD column (available from Chiral Technologies in Exton, Pa.) with a mobile phase consisting of 90% hexane/10% IPA to determine the enantiomeric excess of the alcohol produced. The chiral alcohol formed from the chlorinated ketone eluted at 14.6 min. The enantiomeric excess (ee) % was calculated using the following formula:

$$([(R)-(S)]/[(R)+(S)]) \times 100).$$

What is claimed is:

1. A process for the preparation of a compound of Formula I

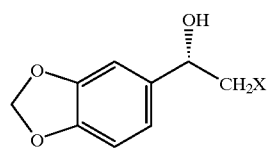

comprising the step of culturing a microorganism *Rhodotorula piliminae*, in a nutrient medium containing assimilable sources of nitrogen and carbon and a substrate compound of Formula II,

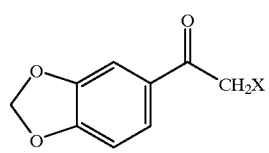

wherein X is F, Cl, Br, or I.

2. The process of claim 1 wherein X is Cl.

* * * * *